United States Patent
Selck et al.

(10) Patent No.: US 12,215,385 B2
(45) Date of Patent: Feb. 4, 2025

(54) SYSTEM AND METHOD FOR PROVIDING BIOLOGY-BASED ANTI-TAMPER

(71) Applicant: NORTHROP GRUMMAN SYSTEMS CORPORATION, Falls Church, VA (US)

(72) Inventors: David A. Selck, Merritt Island, FL (US); Om Prakash, McLean, VA (US); Lito Medalle, Rolling Meadows, IL (US)

(73) Assignee: NORTHROP GRUMMAN SYSTEMS CORPORATION, Falls Church, VA (US)

( * ) Notice: Subject to any disclaimer, the term of this patent is extended or adjusted under 35 U.S.C. 154(b) by 650 days.

(21) Appl. No.: 16/120,987

(22) Filed: Sep. 4, 2018

(65) Prior Publication Data
US 2020/0071758 A1   Mar. 5, 2020

(51) Int. Cl.
C12Q 1/68     (2018.01)
C12Q 1/04     (2006.01)
C12Q 1/6876   (2018.01)

(52) U.S. Cl.
CPC ............. *C12Q 1/6876* (2013.01); *C12Q 1/04* (2013.01)

(58) Field of Classification Search
CPC ....................................................... C12Q 1/68
See application file for complete search history.

(56) References Cited

U.S. PATENT DOCUMENTS

| 9,919,512 B2* | 3/2018 | Jung .................... C12Q 1/68 |
| 2004/0166520 A1* | 8/2004 | Connolly ............. C12Q 1/6825 435/6.12 |
| 2006/0121181 A1* | 6/2006 | Sleat .................... E05G 1/14 427/7 |
| 2006/0286569 A1* | 12/2006 | Bar-Or .................... C12Q 1/68 435/6.11 |

(Continued)

FOREIGN PATENT DOCUMENTS

| WO | WO-2016114808 A1 * | 7/2016 | ............. C12Q 1/686 |
| WO | WO-2019040871 A1 * | 2/2019 | ......... G11C 13/0019 |
| WO | WO-2019140101 A1 * | 7/2019 | ......... B05B 12/1418 |

OTHER PUBLICATIONS

Pakendorf, Combinatorial DNA barcoding for security applications Thesis submitted for the degree of Master of Philosophy at the University of Leicester, 2015.*

(Continued)

*Primary Examiner* — Aaron A Priest
(74) *Attorney, Agent, or Firm* — KATTEN MUCHIN ROSENMAN LLP

(57) ABSTRACT

A system for biology based anti-tamper and a method for detecting a tampering activity to an object using biological materials are provided. The system includes a biological medium that includes a biological member such as deoxyribonucleic acid (DNA), ribonucleic acid (RNA), and/or live or hibernating organism. The biological medium is applied to a portion of an object that is required to monitor whether any tampering may have occurred. The biological member is engineered to change its state when exposed to a stimulus. Upon suspicion, the state of the biological member is examined to find if there is any change of state. The biological member is capable of being barcoded, which provides an extra security measure.

14 Claims, 6 Drawing Sheets

(56) References Cited

U.S. PATENT DOCUMENTS

| | | | |
|---|---|---|---|
| 2012/0135413 A1* | 5/2012 | Brown | C12Q 1/6876 435/6.12 |
| 2015/0141264 A1* | 5/2015 | Jung | C12Q 1/68 506/2 |
| 2020/0071774 A1* | 3/2020 | Paul | C12Q 1/686 |

OTHER PUBLICATIONS

BarCode of Life, available at https://www.ncbi.nlm.nih.gov/genbank/barcode/, accessed Jun. 6, 2022.*

* cited by examiner

SYSTEM AND METHOD FOR PROVIDING BIOLOGY-BASED ANTI-TAMPER

BACKGROUND

Anti-tamper technologies span two broad and general categories: those which actively prevent tampering, and those which alert to the fact that tampering may have occurred. A version of this type of device used in military hardware often is based on microelectronics technologies with a wide array of potential application areas. These microelectronic devices may be used to erase programmed logic, if probed inappropriately, as a result leaving nothing to reverse engineer, or simply log and report questionable activities.

A version of this type of device is commonly included in consumer electronics where a seal is placed over a critical joint involved in the disassembly of a piece of equipment. A broken seal typically voids any manufacturer warranty as it indicates that the device has been tampered with and any behavior outside of specification may have been caused by the user. There are a variety of different devices such as this including one commonly used on phones which changes color if fully immersed in water. Such an action is another behavior which typically voids any warranty.

One issue with techniques such as these is that they are overt, and in the case of the microelectronics, they typically require constant power. Overt technologies have their place as they provide rapid and direct feedback with regards to tampering. The feedback includes either the strip is broken or not or a signal is received regarding likely tampering activity. Overt technologies also have their drawbacks, however, as it is much easier to circumvent something that is known. Covert technologies, then, when used complementary to or in place of overt technologies can be much more effective.

There have been studies in biochemistry space to understand and tweak simple organisms for applications, but these studies are far outside of anti-tamper field. For instance, base technologies which are used in both deoxyribonucleic acid (DNA) and ribonucleic acid (RNA) solutions have been around for well over 30 years. Base technologies which may be used to generate an engineered life form are newer, and have been developed within the last five to twenty years, although as in the case of the DNA and RNA, such technologies have not been applied to anti-tamper functionality.

The current state of the art for anti-tamper is typically performed using microelectronics. The techniques are vast and, therefore, no specific implementations will be described here. Such techniques, however, span passive sensing, active surveillance, encryption, environmental monitoring, etc. Anti-tamper using microelectronic solutions is sensible as nearly anything can be performed. The drawbacks of such solutions include that they are expected and often highly overt. The advantage of using biologics for anti-tamper is they are covert and unexpected and, therefore, are more likely to go unseen and catch inappropriate behavior.

SUMMARY

Embodiments include a system that implements a new biology-based methodology which may be used to detect tampering. Anti-tamper technologies are critical as measures to protect against tampering and reverse engineering. Embodiments overcome the disadvantages of overt anti-tamper technologies and other disadvantages described above. These and other advantages may be achieved, for example, by a biological system for detecting a tampering activity of an object. The biological system includes a biological member including at least one biological material that is engineered to change its state when exposed to one or more stimuli, and a medium that contains the biological member and holds the biological member in contact with or located within the object. A change of the state of the at least one biological material is detectable when tampering activity of the object has occurred.

The at least one biological material may include deoxyribonucleic acid (DNA), ribonucleic acid (RNA), and/or live or hibernating organism.

The at least one biological material may include a DNA fragment and the medium may be a form of a coating that is configured to cover a portion of the object that will be affected if the object is disassembled. The DNA fragment may be engineered to have a barcode.

The at least one biological material may include a RNA strand and the medium may be configured to be formed on a portion of the object in which the RNA strand is not exposed to the one or more stimuli unless tampering activity of the object occurs. The RNA strand may include a plurality of fixed domains and a plurality of variable domains and the variable domains may be barcoded. Among the plurality of fixed domains, two fixed domains may be closer together, and another fixed domain may be distant away from the two fixed domains.

The at least one biological material may include live or hibernating organisms and the medium may be configured to be disposed in a portion of the object in which the live or hibernating organism is not exposed to the one or more stimuli unless tampering activity of the object occurs. The live or hibernating organism may be engineered to have a barcode.

These and other advantages may also be provided, for example, by a method for detecting a tampering activity to an object. The method includes forming a biological medium on the object, and examining a state of the biological medium to detect any change in the state. The biological medium includes at least one biological member that is engineered to change its state when exposed to a stimulus, and a change of the state of the biological medium is detectable. The method may further includes barcoding the at least one biological member.

The at least one biological member may include DNA fragment and said forming the biological medium may include forming the at least one biological member on a portion of the object that will be affected if the object is disassembled. Said examining the state of the biological medium may include applying dye to the biological medium.

The at least one biological member may include RNA strand and said forming the biological medium may include forming the at least one biological member on a portion of the object in which the RNA strand is not exposed to the stimulus unless tampering activity of the object occurs. Said forming the biological medium may further include forming a plurality of fixed domains and a plurality of variable domains in the RNA strand. Among the plurality of fixed domains, two fixed domains may be closer together, and another fixed domain may be distant away from the two fixed domains. The variable domains may be barcoded. Said examining the state of the biological medium may include evaluating degradation of the RNA strand.

The at least one biological member may include a live or hibernating organism and said forming the biological medium may include disposing the at least one biological member in a portion of the object in which the live or hibernating organism is not exposed to the stimulus unless tampering activity of the object occurs. Said examining the state of the biological medium may include quantifying metabolic activity of the organism.

These and other advantages may also be provided, for example, by a system for detecting a tampering activity to an object. The system include a biological medium that includes a biological member formed on the object, and a medium for holding the at least one biological member to the object. The biological member includes at least one biological material that is engineered to change its state when exposed to one or more stimuli and is capable of being barcoded. A change of the state of the at least one biological member is detectable.

The system may further include a plurality of mediums. The at least one biological material may include a DNA fragment, a RNA strand, and/or live or hibernating organisms. The DNA fragment may be suspended in a first one of the plurality of mediums that is configured to be formed on the object as a coating that is configured to cover a portion of the object that will be affected if the object is disassembled. The RNA strand may be suspended in a second one of the plurality of mediums that is configured to be formed on a portion of the object in which the RNA strand is not exposed to one or more of the one or more stimuli unless tampering activity of that portion of the object occurs. The live or hibernating organisms may be suspended in a third one of the plurality of mediums that is configured to be disposed in a portion of the object in which the live or hibernating organism is not exposed to one or more of the one or more stimuli unless tampering activity of that portion of the object occurs.

BRIEF DESCRIPTIONS OF DRAWINGS

DETAILED DESCRIPTION

Figure 1A:
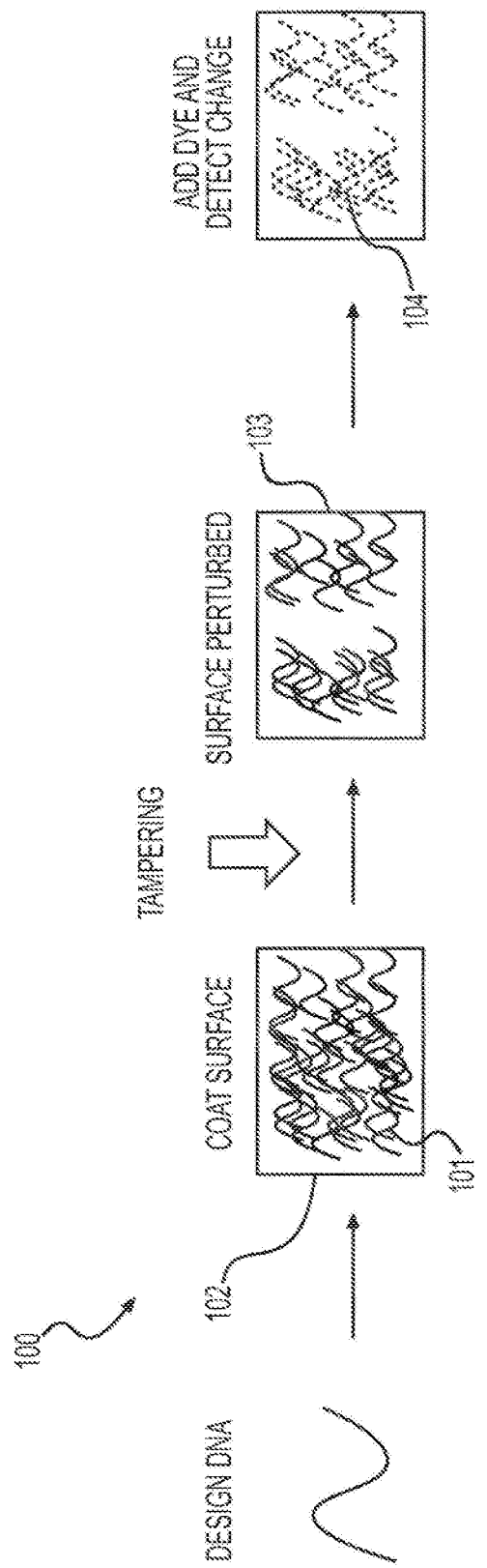
FIGS. 1A and 1B illustrate an embodiment of a system and method for providing biology-based anti-tamper using DNA fragment.

It is to be understood that the figures and descriptions of the present invention may have been simplified to illustrate elements that are relevant for a clear understanding of the present invention, while eliminating, for purposes of clarity, other elements found in a typical mobile applications architecture or typical method for sharing data. Those of ordinary skill in the art will recognize that other elements may be desirable and/or required in order to implement the present invention. However, because such elements are well known in the art, and because they do not facilitate a better understanding of the present invention, a discussion of such elements is not provided herein. It is also to be understood that the drawings included herewith only provide diagrammatic representations of the presently preferred structures of the present invention and that structures falling within the scope of the present invention may include structures different than those shown in the drawings.

Embodiments use biological material, whether a living organism or simply a collection of or singular biomolecules to aid in detection of tampering. There are a variety of means under which embodiments may be implemented as organism growth, death, and hibernation characteristics are governed by environment, and biomolecules can have metered response to environmental stimuli. For example, a hibernating anaerobic bacterium may be used to detect whether a hermetically sealed chamber has been opened and exposed to oxygen. If that bacterium was exposed to oxygen, the toxic environment would kill the organism with no overt feedback to the person who tampered with the device, while someone seeking to detect tampering would learn of the tampering by learning that the organism was dead.

Another embodiment may include an environmentally degradable molecule, such as RNA, in a compartment which must remain sealed. RNA is a cheap and easily produced biomolecule which degrades rapidly if exposed to the environment. Due to evolution, extracellular RNAses (enzymes which decompose RNA) are ubiquitous (realistically existing on any unbleached surface) and, therefore, if a chamber containing an RNA is opened, the RNA will be exposed to RNAses which degrade the contained RNA(s), a degradation which can be quantified using well-developed biochemical techniques.

A purpose of embodiments described herein is to define ways in which biologics can be used to covertly survey tampering activity. An advantage to using biological materials for tamper detection, as opposed to other technologies, is the ubiquity of such biological materials. Organisms such as bacteria are pervasive in nearly all environments, and bio-chemicals such as DNA, RNA, or proteins are even more common. Therefore, even if such anti-tamper materials were discovered in the course of a careful assessment by an unsavory actor, it is likely that the presence of such materials would be flagged as suspicious by the actor.

Another advantage of biology-based anti-tamper technology of the present invention is that such technology is covert and is not easily discovered during tampering activities. This advantage may be demonstrated through the following three exemplary situations.

In a first situation, anti-tamper functionality is a common mission or is system requirement for a piece of equipment. Requirements include the need to have covert anti-tamper functionality and that the anti-tamper functionality provides means through which tampering activity can be easily detected and quantified when necessary, such as when equipment or information is unintentionally compromised. The equipment is not sealed and a concern is that it may be disassembled.

In this situation, an anti-tamper apparatus including DNA may be used to examine whether the equipment has been disassembled. A DNA fragment is designed, and is evenly spread on areas which would require handling in order to dismantle the piece of equipment. This area may be, for example, a critical joint in the equipment or a fastening member. As DNA is ubiquitous in almost any environment, it is unlikely that it would be noticed that a specifically designed DNA fragment is spread on the area. The DNA fragment may have a pattern such as a certain type of alignment of DNAs or uniformity of the coating of DNA fragment. Upon disassembly, the DNA fragment becomes disturbed and the pattern of the DNA fragment applied on the area changes. This change may be detected by spraying an intercalating dye on suspect areas and checking for fluorescent activity. A change is detected, and appropriate action can be taken.

Figure 1B:
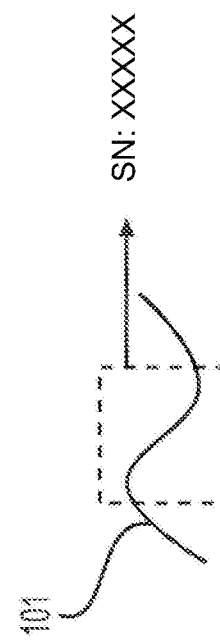

With reference now to FIGS. 1A and 1B, shown is a system and method 100 for providing biology-based anti-tamper using DNA fragments. Referring to FIG. 1A, a DNA fragment 101 is engineered as a biological member to change its state when exposed to a stimulus such as physical handling. DNA fragment 101 may be substantially evenly applied on an area or surface 102 (the "coat surface") that is likely to be touched during disassembly or other tampering. Upon being touched or otherwise tampered, the state of DNA fragment 101, such as a pattern or uniformity of the DNA fragment 101, may be changed or perturbed. This is illustrated by the perturbed DNA fragment 103 shown in FIG. 1A. Detection of any changes in the DNA fragment spread on the area, i.e., of the perturbed surface 103, may be achieved by applying a dye such as an intercalating dye. When in contact with an intercalating dye (such as ethidium bromide), DNA fluoresces brightly. These intercalating dyes when not in contact with DNA are in a physical conformation that prevents them from fluorescing. Dye is applied to the area (dyed surface 104) to detect any changes of the state of DNA fragment. Upon excitation, e.g., by the exposure of the dyed surface 104 with blue ultraviolet light, the perturbed DNAs may emit green light. By observing a pattern of the green light, it can be determined whether the pattern or uniformity of the DNA coating 102 is changed. If the pattern of the DNA coating 102 is changed, system 100 may indicate that the equipment may have been disassembled or otherwise tampered.

Referring to FIG. 1B, DNAs applied on the area are barcoded. Even in a circumstance in which the DNA coating was discovered by an unsavory actor and a new coating of DNA was applied by the actor to attempt to hide the disassembly or other tampering activity, the barcode of the DNA can be checked through, e.g., sequencing, polymer chain reaction (PCR), or a combination thereof to determine if the DNA is the original, applied anti-tamper DNA and to determine if there has been disassembled or other tampering activity. DNAs applied to the area or surface 102 may be interrogated and the internal barcode may be compared with the barcode that is expected. If it is discovered that the DNA barcode is different from the original barcode of DNA coating 101 which was applied, either differing in sequence or relative concentrations of a mix of DNA sequences, it proves that there was a disassembly or other tampering activity.

Figure 1C:
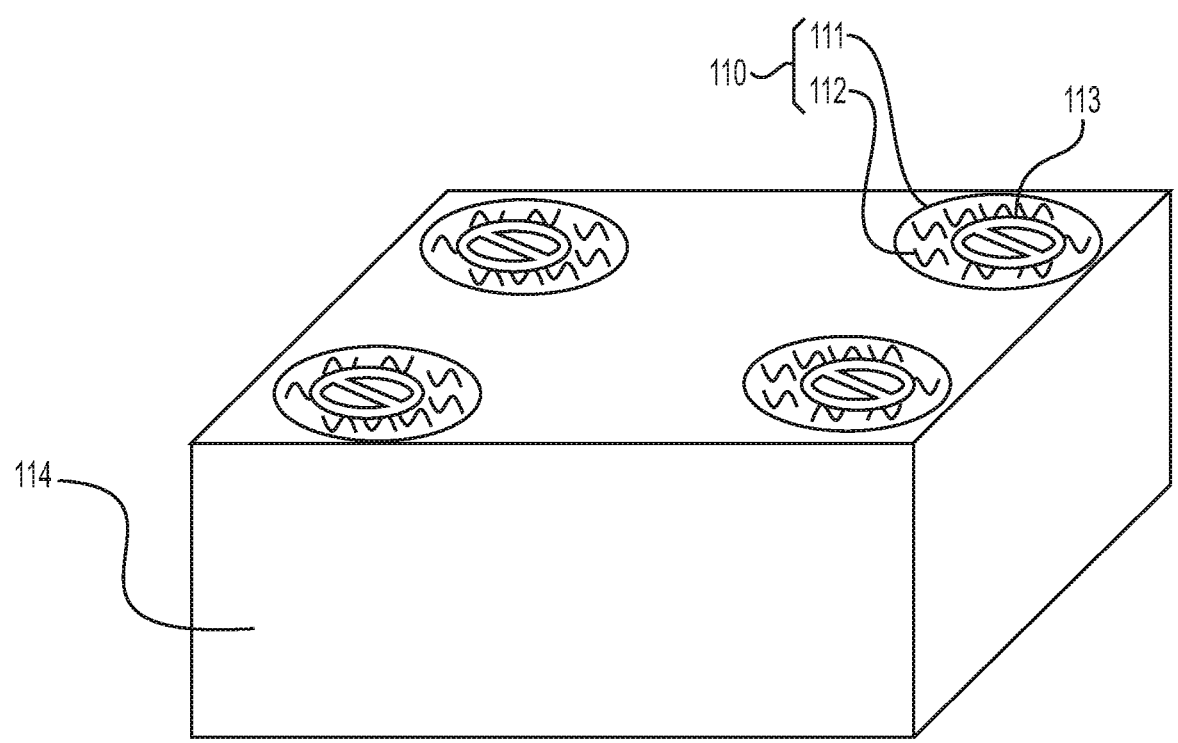
FIG. 1C illustrates an exemplary application of an embodiment of a system and method for providing biology-based anti-tamper using DNA fragment.

FIG. 1C illustrates the exemplary situation above in which an anti-tamper apparatus 110 including DNA fragments 112 is installed on an equipment 114 that requires an anti-tamper functionality. The equipment 114 has fastening members 113 through which the equipment 114 may be disassembled. The apparatus 110, which includes a medium 111 containing DNA fragments 112, is applied around the fastening members 113. The medium 111 is in a form of a coating that is configured to cover the fastening members 113 that will be affected if the equipment is disassembled.

In applications, DNA may not be suspended in any specific medium. DNA is a hearty polymer that has relatively high stability in a broad range of environments. The medium for the DNA may be in application to a surface. The suspension solution or medium for DNA may be water (e.g., deionized water) or may include a solution such as a buffered Tris(Hydroxymethyl) aminomethane (TRIS) solution. To ensure stability the medium may include a stabilization agent such as trehalose.

In a second situation, a device includes a removable computer chip. There is concern that the chip may be removed in an attempt to reverse engineer the chip's functionality or to damage the device. There is a requirement to include covert detection technologies to provide awareness as to whether or not the chip is or has been removed.

In this situation, an embodiment of a system for providing biology-based anti-tamper including RNA may be used to detect whether the chip has been removed or otherwise tampered. An area underneath the chip may be carefully cleaned and then a coating of RNA is applied which has been engineered in such a way that degradation can be easily quantified. Upon suspicion that the chip has been removed, the RNA coating may be examined, e.g., using reverse transcription polymer chain reaction (RTPCR). If the chip has been removed, or if there has been tampering with the chip, the examination of the RNA may quantify and reveal more degradation of the RNA than would be expected without removal or tampering. To determine whether the degradation is more than would be expected, the result of the examination may be compared with a controlled degradation of RNA. If the degradation is determined to be greater than the controlled degradation by more than a pre-determined threshold, system for providing biology-based anti-tamper including RNA may conclusively determine that the chip had been removed.

Figures 2A, 2B:
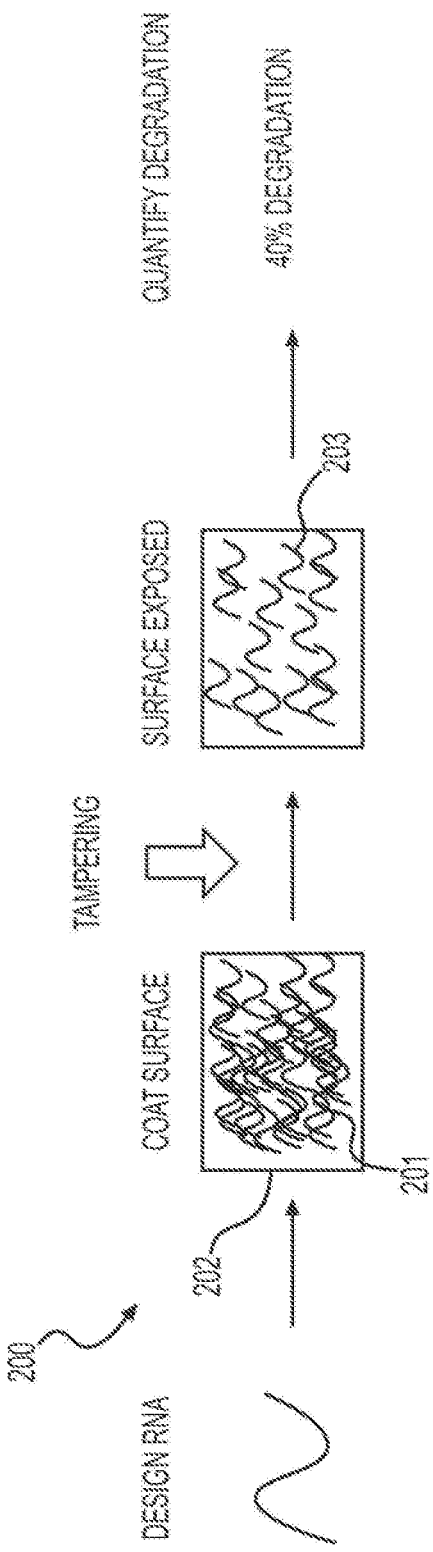
FIGS. 2A and 2B illustrate an embodiment of a system and method for providing biology-based anti-tamper using RNA.

With reference now to FIGS. 2A and 2B, shown is system and method 200 for providing biology-based anti-tamper using RNA. Referring to FIG. 2A, a coating of RNA 201 is applied to or otherwise formed on coat surface 202. In an embodiment, coat surface 202 may be a substrate or other surface ordinarily covered by another object (not shown), such as a computer chip. In this configuration, the RNA 201 is ordinarily covered by the object (e.g., computer chip) and is not exposed to the environment unless that object is removed. After RNA coating 201 is applied to the coat surface 202, the covering object is installed on top of the coat surface 202. When the object (e.g., the chip) is removed or otherwise sufficiently tampered with so that the coat surface 202 is uncovered, the RNA coating 201 is exposed to the environment (which acts as a stimulus to the RNA), and the RNAs begin to degrade. An amount or rate of degradation of RNA 203 may be evaluated by RTPCR. If the observed degradation is higher than a predetermined or expected degradation, it may be determined that the object (e.g., the chip) has been removed or otherwise tampered.

Referring now to FIG. 2B, shown is an embodiment of system and method 200 for providing biology-based anti-tamper using RNA that includes barcodes. RNAs deposited or otherwise formed on the surface 202 of the object may be barcoded. Some domains of the RNA strand may be used for barcoding. In their simplest implementation the barcodes may be used to ensure that each domain receives a slightly different barcode. When using barcoding, it is necessary that no strand of RNA is used more than once, which provides additional security. Upon suspicion, the RNAs on the coat surface 202 may be interrogated and internal barcode of the RNAs is compared with the expected barcode (e.g., barcode of the RNA coating 201). If it is discovered that the RNA barcode that is present on the coat surface 202 is different from the original barcode of the RNA 201 which was applied to the surface 202, then the chip has been removed or otherwise tampered. Barcoding not only acts as an extra security measure, but it also provides a secondary covert serial number which may be used to track equipment.

Figure 2C:
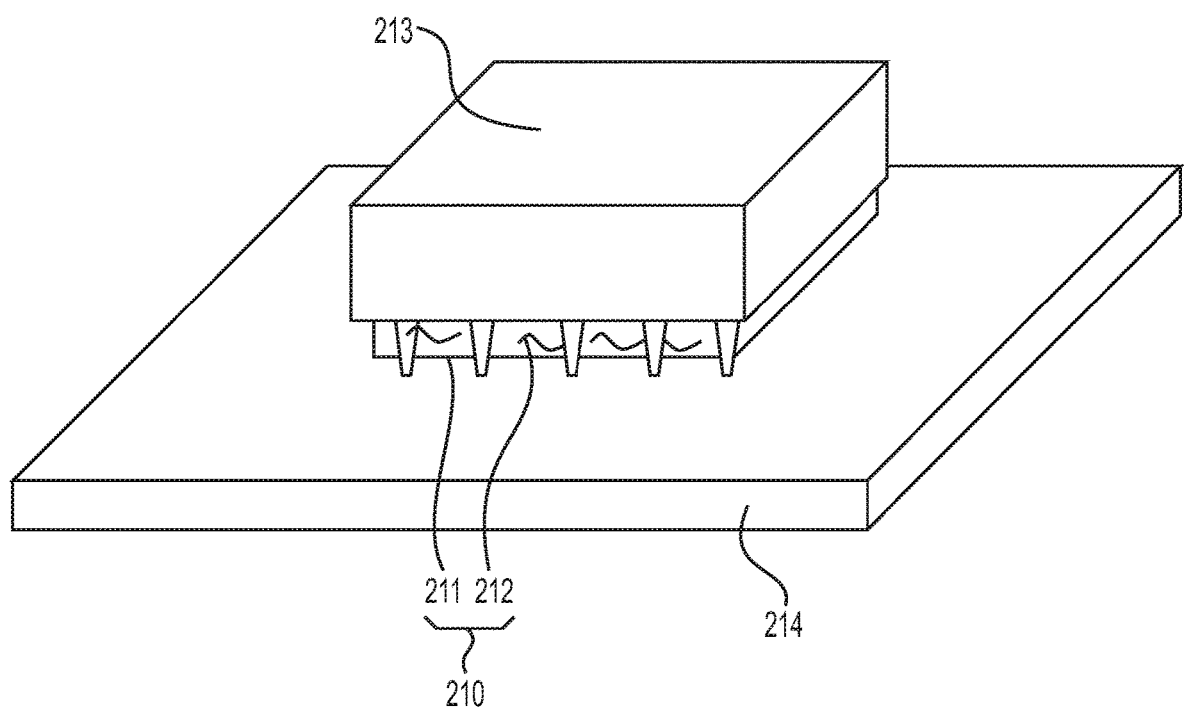
FIG. 2C illustrates an exemplary application of an embodiment of a system and method for providing biology-based anti-tamper using RNA.

FIG. 2C illustrates the second exemplary situation in which an anti-tamper apparatus 210 including RNA strand 212 is installed on a computer chip 213 that requires covert detection technologies to provide awareness as to whether or not the chip has been removed. The apparatus 210, which includes a medium 211 containing RNA strand 212, is formed underneath the chip 213 that is installed on a board 214 such as a printed circuit board. If the chip 213 is removed from the board 214, the medium 211 containing RNA strand 212 will be exposed to an environment, which may cause degradation of RNA.

RNA may have similar constraints as the DNA. In order to improve stability, the surfaces to which RNA is applied may be cleaned with a suitable solvent to remove RNAses. After the cleaning, the RNA may be suspended in an RNAse free buffer such as TRIS in RNAse free water. The medium may also include stabilization agents such as trehalose.

In a third situation, e.g., on a piece of equipment under contract, the customer is mandating that covert anti-tamper functionality be included in a hermetically-sealed portion of the equipment. In this scenario, the anti-tamper functionality (a) must be able to provide information as to whether or not the hermetically-sealed portion of the equipment was opened and (b) must work without any power source.

In this situation, an embodiment of a system for providing biology-based anti-tamper may include living organisms to detect changes in environment. For example, an anaerobic bacterium can be used to determine whether the hermetically sealed portion of the equipment has been opened. Living organisms, or colonies thereof, may be engineered to respond to a variety stimuli including light, atmospheric change, physical touch, and temperature change. The engineered living organism is included or suspended in a solution or other amenable medium and the complex is then placed within the hermetically-sealed chamber. After some time, the chamber is opened and the organism is examined. If it is discovered that the bacteria have all died or had specific metabolic alterations, such a fact is an indication that the hermetically-sealed chamber has been opened in the past and exposed, e.g., to oxygen (or light, or temperature change, or touch). The metabolic activity of the bacteria may also be investigated; such metabolic activity may, e.g., indicate that prior to death the bacteria were responding to an increase in oxygen concentration or other environmental stimulus confirming suspicions that the chamber had been opened to the ordinary environment. A variety of anaerobic bacterium among other living organisms may be used, including, e.g., *Actinomyces, Bacteroides, Fusobacterium, Peptostreptococcus, Porphyromonas, Prevotella, Propionibacterium*, and *Veillonella* bacterium.

Figure 3A:
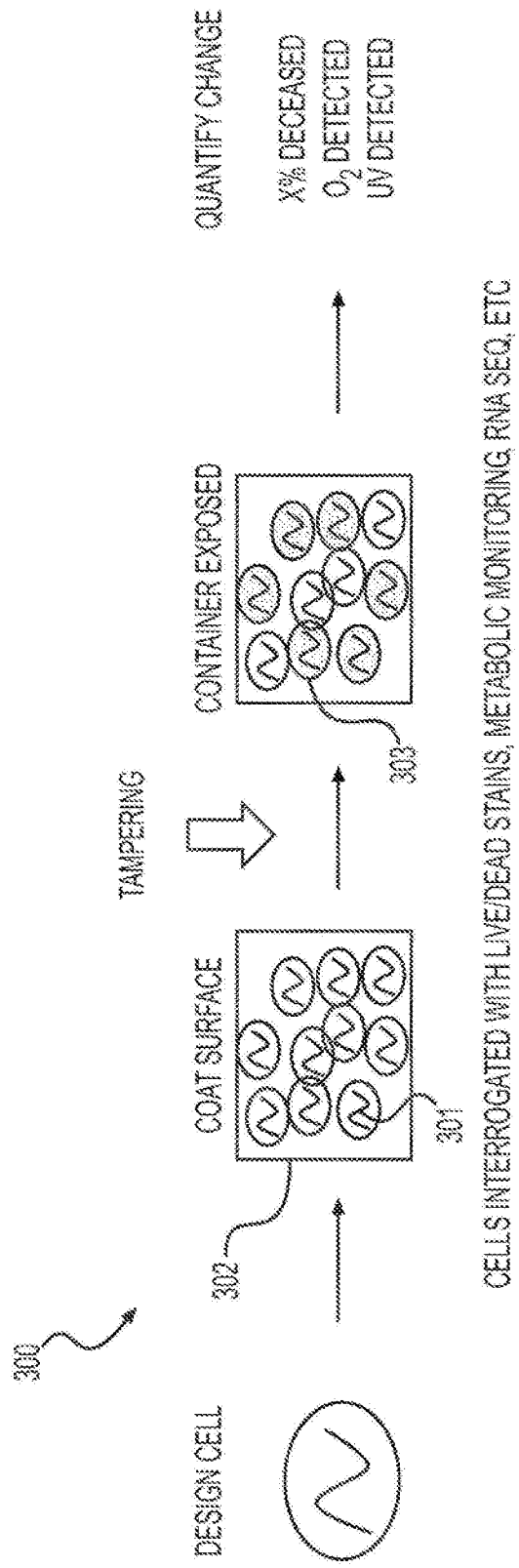
FIGS. 3A and 3B illustrates an embodiment of a system and method for providing biology-based anti-tamper using living organisms.
Figure 3B:
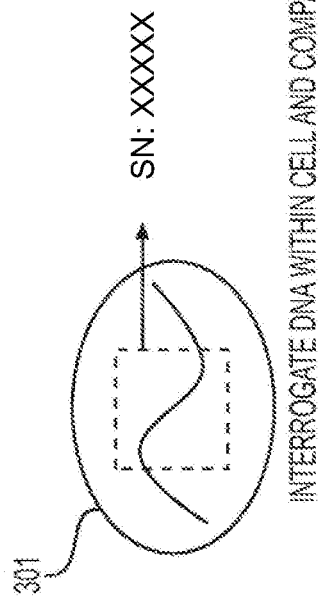

With reference now to FIGS. 3A and 3B, shown is an embodiment of system and method 300 for providing biology-based anti-tamper using living organisms. Referring to FIG. 3A, organisms 301 are engineered to respond to one or more stimuli that can change the state of the medium. The organisms 301 may be suspended in a solution or other medium and the solution or other medium disposed inside an object 302, such as a hermetically-sealed chamber or container, in which the organisms will not be exposed to the one or more stimuli. While the organisms 301 stay inside the object, the organisms 301 are protected from the stimuli. However, once the object is opened or the hermetic-seal otherwise broken, the organisms 301 may be exposed to the stimuli, resulting in changes of the state of the organisms 301. The change of state may be quantified by interrogating metabolic activity of the organisms 301, such as an amount of death 303, which may show whether the organism was exposed to, for example, oxygen or ultraviolet (UV) light or other stimuli to which the organism 301 is engineered to respond.

Referring to FIG. 3B, the organism 301 may be engineered to contain a specific barcode which would serve all of the same functions as described above with reference to FIGS. 1B and 2B. In this case, DNA within the nucleus of the organism present in the object 302 may be interrogated, and the barcode is compared with the barcode that is expected of the organism 301. If it is discovered that the barcode is different from the original barcode of the organism 301 that was disposed inside the object 302, it proves that the object 302 has been opened or the hermetic-seal otherwise broke.

Figure 3C:
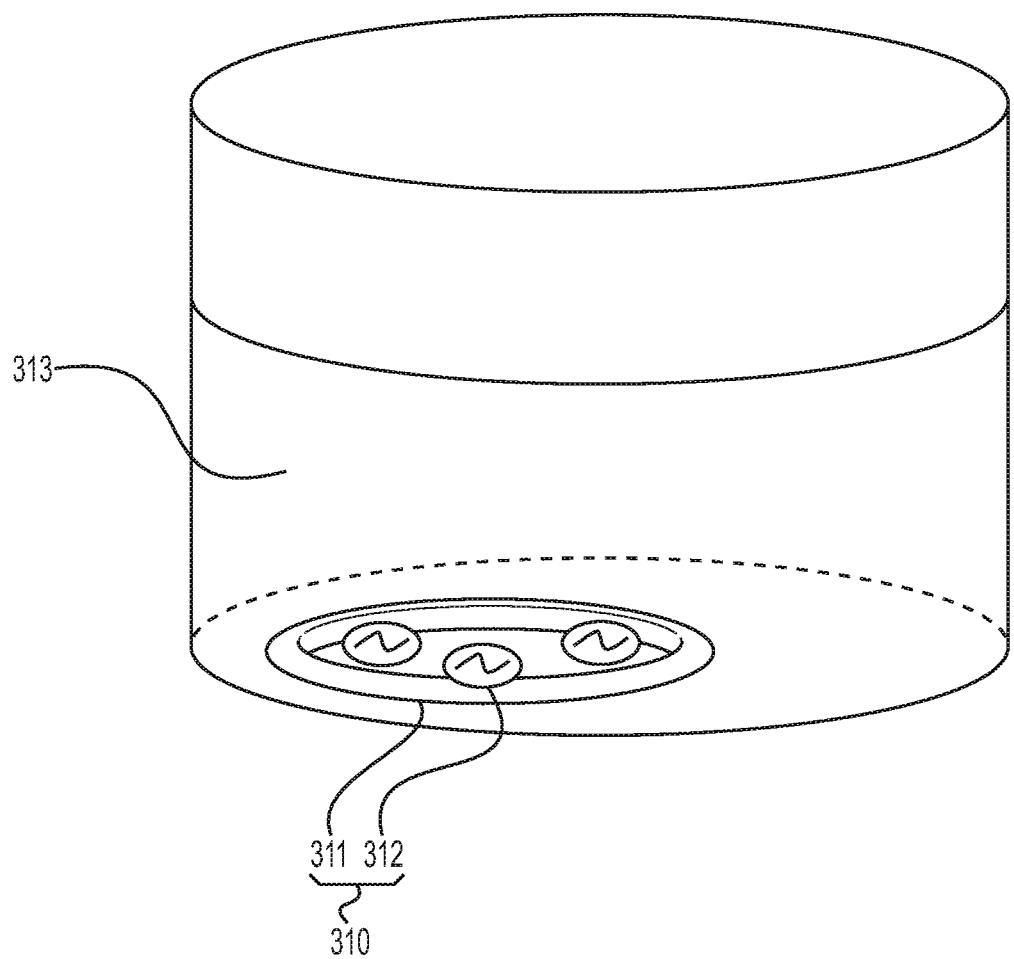
FIG. 3C illustrates an exemplary application of an embodiment of a system and method for providing biology-based anti-tamper using living organisms.

FIG. 3C illustrates the third exemplary situation in which an anti-tamper apparatus 310 including live or hibernating organisms 312 is disposed inside a hermetically-sealed chamber 313. The apparatus 310, which includes a medium 311 containing live or hibernating organisms 312, is disposed on a bottom surface of the hermetically-sealed chamber 313. If the chamber 313 is opened, the medium 311 containing the organisms 312 will be exposed to an environment, which may result in changes of the metabolic state of the organisms.

The hibernating and/or living organisms may need a medium in which the organisms are suspended. The presence of a medium may help to make the conclusiveness of any derived examination as to whether an organism is dead, alive, metabolically altered, etc. As long as the organisms in the system maintain stability, the medium may not be required. This medium may include any standard growth and/or storage medium commonly used within the biology field such as for example agar. In applications, the organisms may not be enclosed within a secondary container inside of the sealed environment, as the organisms need to be exposed to this sealed environment. The medium may be hidden in a plain site by concocting the medium to have the same consistency of, for example, a grease which could be easily mistaken as a sealant or lubricant.

Anaerobic bacteria may be suitable for determining whether or not the enclosed system has been exposed to oxygen. In order to have response to other stimuli including touch, light, etc., the hibernating and/or living organisms may include a variety of other organisms including bacteria in the *Streptomyces* and *Escherichia Coli* families among a wide variety of other organism types including those which are commonly used in synthetic biology such as yeast and archaea.

Inventive concepts of the embodiments described herein include the usage of a technology which would normally not be considered for anti-tampering systems. In any covert activity there is always a desire to stay one step ahead of the bad actors to ensure that methods and techniques are not discovered. Standard techniques therefore, even if they are well engineered, are less likely to succeed in the end as they can still be evaded.

The embodiments described herein are also inventive in that the techniques used are not easy to detect even if one looks for them or suspects they are present. In the case of DNA, for example, intercalating dyes can alert one to the presence of DNA. However, the time and effort associated with determining the barcode of the DNA can be significant unless it is already known. This is because all rapid techniques require a set of predefined "amplification primers" which are specific to that strand. The covert nature becomes even more pronounced with RNA as there is no immediate test which can be performed to determine the presence or absence of RNA. Therefore, the use of RNA would only be discovered if it was specifically sought after, an exercise which would destroy what RNA was used in the first place.

A benefit of the embodiments and techniques described herein overall is that all versions may be used simultaneously. Therefore, it is not a requirement to only choose one technique. For instance, the DNA and RNA can be mixed giving both a rapid detection technique (for example, intercalating dye) with a quantitative measure of exposure to the environment (for example, quantification of RNA degradation).

In simplest implementations, embodiments involve designing and manufacturing a strand of ribonucleic acid (RNA) with a known sequence. Within the strand of RNA there is at a minimum three (3) fixed domains and any number of variable domains. The variable domains of the RNA strand may be specifically used for barcoding. The barcodes could denote any number of things. However, in their simplest implementation the barcodes would be used to ensure that each component (domain) received a slightly different barcode. This would not only act as an extra security measure as no strand would be used more than once, it would also act as a secondary covert serial number which could be used to track equipment. The function of the (minimum) three (3) fixed domains within the RNA strand would be used to track degradation of the nucleic acid. Degradation of RNA occurs stochastically. This means that longer strands of nucleic acid are much more likely to be degraded than smaller strands (more sites which can be attacked). As the technique used to determine whether or not the RNA molecule is degraded, which typically involves reverse transcription followed by polymerase chain reaction (RTPCR), functions by duplicating a section of a nucleic acid in between two fixed regions. Therefore, placement of the three (3) fixed domains will be done in such a way so that two (2) fixed domains are close together and the third fixed domain is some distance away. Placing the domains in this manner ensures that there is a duplication region of shorter length (smaller strand), which will be more robust to degradation, and a longer region which will be much less robust to degradation. By comparing the differences in the quality of the two lengths of the strand which are easily detectable using RTPCR, one can derive the degradation state of the RNA and infer as to whether the compartment was opened.

The fixed domains may be fixed in both relative positions such as in (x, y) coordinates and distances separating the three domains, and length in addition to having a known sequence that can vary by application as a form of barcoding. As far as the variable domains are concerned, the variable domains may be moved around. If the variable domains are altered, the system may need to be recalibrated after altering the variable domains, as sequence denotes structure which can alter the read-out chemistries and half-lives of the RNA. Therefore, as far as parameters in the variable domain are concerned, there may not be only one variable parameter such as a position, but there may be other variable parameters that may characterize the variable domain. The sequence may contribute to the quantification of decay, so the sequence needs to be known and qualified.

A second implementation may involve using engineered anaerobic bacteria to determine whether a hermetically sealed chamber was opened. In this instance, the chamber would need to be hermetically sealed as exposure to oxygen is toxic and deadly to anaerobic bacteria. Therefore, if the chamber were exposed to oxygen the bacteria lying within would perish, which can be rapidly detected through the use of a live/dead stain. The bacteria could also be engineered to contain a specific barcode which would serve all of the same functions as described in the previous paragraph. This would be a difficult to detect and evade mechanism as the bacteria could be designed to reside in a dormant state with little propagation which would keep the bacteria from forming large visible colonies, and once the bacteria have died they must be replaced with the same bacteria as they were specifically barcoded. A second function that this type of anti-tamper mechanism could provide is that of silent monitor to changes in environment. The bacteria or other suitable organism could be engineered to detect changes in the environment and respond according to the stimulus. This is something that could be tracked through monitoring the RNA output and metabolic activity of the cells. This extra functionality would allow the organism to act as sentinel in situations where a hermetically sealed chamber was opened, and simple detection of oxygen was insufficient. In this type of situation it would be extremely difficult to ensure that no environmental stimuli of the bacteria changed and thus detectable things such as light contamination, air mix ratios, heat change, and physical touching could still be detected.

A third implementation may involve the use of specific DNA strands coating surfaces which should not be accessible. DNA is ubiquitous being a part of all living things and, therefore, is not something that would necessarily be considered out of place when present on such surfaces. A second benefit of DNA is that it is a hearty and stable molecule which undergoes relatively little environmental degradation. It still retains, however, the ability to be barcoded much the same as the RNA. Therefore, if the DNA was evenly coated along a component which should not be handled, then it would be easy to detect whether or not the part was touched by observing the DNA uniformity across the surface. This may be easily performed covertly as DNA is invisible in its native form. When in contact with an intercalating dye, however, DNA fluoresces brightly. These intercalating dyes when not in contact with DNA are in a physical conformation that prevents them from fluorescing. When such dyes come in contact with DNA, however, they brightly fluoresce and, therefore, are easily detectable using simple equipment. This may allow for rapid feedback as to whether a surface has been disturbed. This may also be a difficult technique to evade as simply sprinkling DNA over a surface that has been disturbed would be insufficient. As DNA is a complex polymer which can be read, it can be barcoded to be specific to a particular piece of equipment. This barcoding may be as simple as having all pieces of DNA within a piece of equipment be the same (although different from any other strand used in a separate application) or having there be a population of different pieces of DNA at a specific and known distribution. Either method may be rapidly, reliably and simply measured using the polymerase chain reaction with reporter probes designed for each known sequence.

One embodiment provides a biological medium for detecting a tampering activity to an object. The biological medium includes one or more biological members and a medium for holding the one or more biological members to the object. Another embodiment provides an apparatus for detecting a tampering activity to an object. The apparatus includes a biological medium that includes one or more biological members and a medium for holding the one or more biological members to the object.

In an embodiment, one of the biological members includes DNA, and the biological medium including DNA is configured as a coating to cover a portion of an object. The DNA may be barcoded. In another embodiment, one of the biological members includes RNA, and the biological medium including RNA is configured to have one or more domains. At least one of the domains of the RNA may be barcoded. In still another embodiment, one of the biological members includes a live or hibernating organism, and the biological medium is configured as a form of a solution to be applied to an object. DNAs within a cell of the organism may be barcoded. In still another embodiment.

Embodiments also provide a method for detecting a tampering activity to an object. The method includes forming a biological medium on the object, and examining a state of the biological medium. The biological medium may include one or more biological members that may include DNA, RNA and/or live or hibernating organisms. As described above, if the biological member includes DNA, dye may be applied to detect changes of the state of the biological member, such as changes in pattern of a DNA coating. If the biological member includes RNA, degradation of RNA may be evaluated to detect changes of the state of the biological member. If the biological member includes live or hibernating organisms, metabolic activity of the organism may be quantified to detect changes of the state of the biological member.

Depending on the type of solution desired, development costs may vary. However, in practically all cases deployment costs are minimal. The cheapest solution to develop and deploy would be that of a DNA based technique as described above in the first problem and solution. This type of DNA fragment (or population of fragments) could be designed or engineered using a basic understanding of biochemistry and simply verified. Total development time would likely be less than one month. Deployment costs would also be the cheapest as DNA manufacturing capabilities are extremely low cost, and only a minimal amount of product would need to be ordered as it could be replicated using techniques such as PCR extremely cost effectively. Solution such as the RNA technique described above would have a higher development cost as there would be a number of controlled experiments required to verify the degradation rate under specified conditions in the context of any specific RNA strand. Actual deployment costs, however, would be on par with those of the DNA-based technology. The most expensive technique to both develop and deploy would likely be that of the engineered organisms. There would be somewhat significant costs associated with developing the organism with each environmental stimulus requiring some fixed and variable costs associated with development. If there exists a natural specimen which would be able to function as desired, the costs would be significantly less. Deployment costs would also be marginally higher as preparation constraints are slightly different and the costs of growing the colony are higher than the costs of replicating DNA and RNA.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. An anti-tamper system installed at a portion of an object and configured to detect a tampering activity to the object, comprising:
   a biological member including at least one biological material that is engineered to change a state when exposed to one or more stimuli and is engineered such that the change of the state is detectable,
   wherein the biological material includes a ribonucleic acid (RNA) strand including at least three fixed domains and a plurality of variable domains,
   wherein among the at least three fixed domains two fixed domains are located closer to each other within the RNA strand relative to the third fixed domain, thereby rendering sections of nucleic acids of varying size located between the fixed domains,
   wherein exposure of the RNA to one or more stimuli can degrade one or more sections of nucleic acids located between the fixed domains into one or more strands of varying size thereby showing the extent of degradation of the RNA; and
   a medium disposed at the portion of the object to form a coating of the biological member, wherein the medium contains the biological member and holds the biological member in contact with the object, and wherein the medium comprises water and includes trehalose as a stabilization agent to ensure stability of the biological member in the medium.

2. The anti-tamper system of claim 1 wherein the at least one biological material includes a deoxyribonucleic acid (DNA), or a live or hibernating organism.

3. The anti-tamper system of claim 1 wherein the at least one biological material includes a DNA fragment and the medium is a form of a coating that is configured to cover a portion of the object that will be affected if the object is disassembled.

4. The anti-tamper system of claim 3 wherein the DNA fragment is engineered to have a barcode.

5. The anti-tamper system of claim 1 wherein the portion of the object onto which the medium containing the RNA strand is disposed of co is not exposed to the one or more stimuli unless tampering activity of the object occurs.

6. The anti-tamper system of claim 1 wherein the sections of nucleic acids are located within the variable domains of the RNA strand, and the variable domains are barcoded.

7. The anti-tamper system of claim 1 wherein the at least one biological material includes live or hibernating organisms and the medium is configured to be disposed in a portion of the object in which the live or hibernating organism is not exposed to the one or more stimuli unless tampering activity of the object occurs.

8. The anti-tamper system of claim 7 wherein the live or hibernating organism is engineered to have a barcode.

9. An anti-tamper system installed at a portion of an object and configured to detect a tampering activity to the object, comprising:
   one or more biological anti-tamper mediums comprising:
      a biological member formed on the object; and
      a medium that is disposed at the portion of the object to form a coating of the biological member, contains the biological member and holds the biological member in contact with the object, wherein:
      the biological member includes at least one biological material that is engineered to change a state when exposed to one or more stimuli and is engineered such that the change of the state is detectable,
   wherein the biological material includes a ribonucleic acid (RNA) strand including at least three fixed domains and a plurality of variable domains,
   wherein among the at least three fixed domains two fixed domains are located closer to each other within the RNA strand relative to the third fixed domain, thereby rendering sections of nucleic acids of varying size located between the fixed domains,
wherein exposure of the RNA to one or more stimuli can degrade one or more sections of nucleic acids located between the fixed domains into one or more strands of varying size thereby showing the extent of degradation of the RNA; and
the plurality of the variable domains include barcoded variable domains, and
the barcoded variable domains are barcoded differently from each other.

10. The anti-tamper system of claim 9 wherein the at least one biological material of the biological anti-tamper mediums further includes:
a DNA fragment suspended in one of the biological anti-tamper mediums that is configured to be formed on the object as a coating that is configured to cover a portion of the object that will be affected if the object is disassembled; or
live or hibernating organisms suspended in another of the biological anti-tamper mediums that is configured to be disposed in a portion of the object in which the live or hibernating organism is not exposed to one or more of the one or more stimuli unless tampering activity of that portion of the object occurs.

11. The anti-tamper system of claim 1 wherein the at least one biological material is engineered such that the change of the state is detectable by polymerase chain reaction (RTPCR).

12. The anti-tamper system of claim 9 wherein the at least one biological material is engineered such that the change of the state is detectable by polymerase chain reaction (RTPCR).

13. The anti-tamper system of claim 1 wherein the medium comprises Tris (Hydroxymethyl) aminomethane (TRIS).

14. The anti-tamper system of claim 13 wherein degradation of the nucleic acid is tracked using reverse transcription followed by polymerase chain reaction (RTPCR).

* * * * *